United States Patent [19]

Micheli

[11] 4,066,067
[45] Jan. 3, 1978

[54] VIAL STOPPER FOR BLOOD SAMPLING DEVICE

[75] Inventor: Antoine Micheli, Landecy, Switzerland

[73] Assignee: DEMATEX Development & Investment Establishment, Liechtenstein

[21] Appl. No.: 668,795

[22] Filed: Mar. 19, 1976

[30] Foreign Application Priority Data

Mar. 21, 1975 Switzerland .................... 3634/75

[51] Int. Cl.² ........................................... A61B 5/00
[52] U.S. Cl. ............................ 128/2 F; 128/218 DA; 128/220
[58] Field of Search .............. 128/2 F, DIG. 5, 220, 128/221, 218 R, 218 N, 218 NV, 218 D, 218 DA, 218 M, 218 P, 215, 216, 272

[56] References Cited

U.S. PATENT DOCUMENTS

| 3,330,281 | 7/1967 | Visser | 128/218 M X |
| 3,570,486 | 3/1971 | Engelsher et al. | 128/218 M |

Primary Examiner—John D. Yasko
Attorney, Agent, or Firm—Robert E. Burns; Emmanuel J. Lobato; Bruce L. Adams

[57] ABSTRACT

A stopper of an evacuated-tube blood sampling system has a sealing portion fitting in or on the tube and an enlarged external hollow head having a chamber closed by a thin sealing diaphragm which obturates the evacuated tube or vial. Flexible lips on an outer end wall of the head define a narrow central opening receiving and lightly gripping a flexible needle sleeve to pre-assemble the evacuated tube with the needle and its holder without a need to partially perforate the membrane. As the needle sleeve pierces the diaphragm, the needle sleeve is free to buckle within the chamber, thus reducting or cancelling the biasing effect exerted by the buckled sleeve. The sealing portion of the stopper can have annular and axial grooves providing a ventilating system.

20 Claims, 15 Drawing Figures

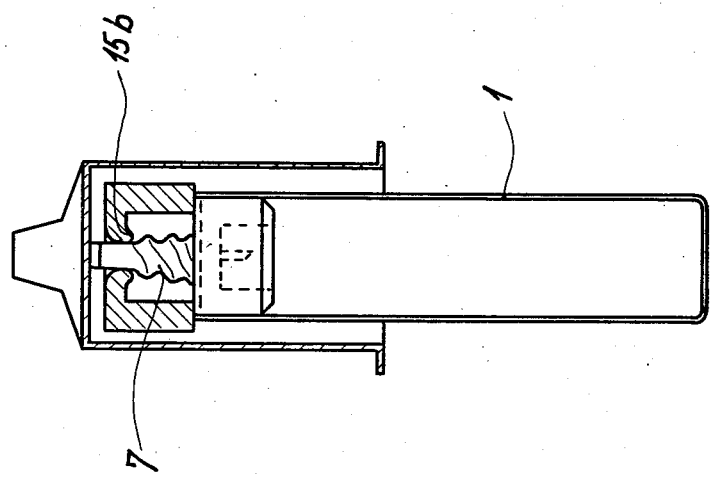
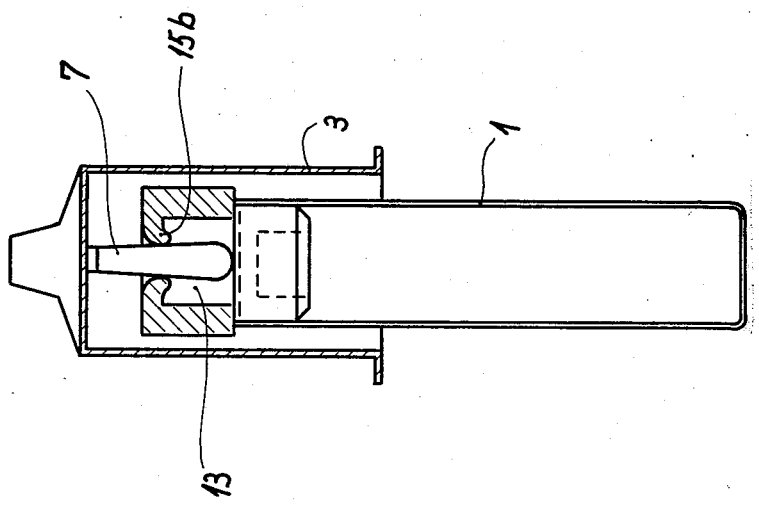

VIAL STOPPER FOR BLOOD SAMPLING DEVICE

BACKGROUND OF THE INVENTION

The invention relates to stoppers for vials, in particular for vials subjected to a controlled pressure, for example evacuated tubes of blood sampling systems.

A known blood sampling system comprises an evacuated tube closed by a stopper and an open-ended needle-holder tube slidably mounted on the tube or its stopper. This needle holder carries a hollow needle having one part protruding axially from the closed end of the holder for pricking into a vein, and another part extending axially within the holder, the latter part being encased in a loose, flexible cover or sleeve. To take a blood sample, the needle is pricked into a vein and the evacuated tube displaced until the needle pierces the membrane, so that blood is sucked into the tube.

However, in practice the use of conventional blood sampling systems often involves difficulties.

Usually, the membrane is quite thick and, just prior to taking a blood sample, when the evacuated tube is fitted into the needle holder, the inner end of the needle must be partly pricked into the membrane in order to pre-assemble the evacuated tube and the needle holder into a blood sampling unit. This is done by sliding the needle holder to a position indicated by a reference mark. However, sometimes the membrane is accidentally perforated at this stage, causing a rise in pressure in the tube which may not then be adequately filled.

After sampling, the filled tube is withdrawn by disengaging it from the needle, but this is made difficult because of the friction of the thick membrane on the needle, and the needle is liable to traumatize the vein. Moreover, the return of the flexible cover over the end of the needle is sometimes delayed, leaving the end of the needle open and allowing blood to be projected onto the head of the stopper, which creates a source of contamination.

SUMMARY OF THE INVENTION

An object of the invention is to provide a stopper for a vial, in particular for use with blood sampling systems, with which it is not necessary to partially perforate the membrane just prior to use, and with which removal of the vial is facilitated as soon as a blood sample has been taken.

A further object is to provide a stopper for an evacuated-tube blood sampling system having a covered needle, with which buckling or other deformation of the cover when the needle perforates the membrane can take place over as great a length as possible and with a reduction or cancellation of the biasing effect exerted by the buckled cover, so that the operator need only lightly press on the vial during blood sampling, or not at all, whereby the risk of hurting the patient or traumatizing the vein is reduced.

According to the invention, a stopper for a vial comprises a hollow body of deformable material having a peripheral wall, a closed inner end wall in the form of a thin sealing diaphragm serving to obturate the vial, and a flexible outer end wall forming at least one flexible lip extending radially inwardly from said peripheral wall and defining a central opening of relatively small section leading into a chamber of larger section defined by said end and peripheral walls.

This stopper preferably has a head which cannot penetrate the vial and a sealing portion extending from said head for providing a sealing fit with the neck of a vial, said chamber being located wholly within said head.

The central opening may be generally circular and may cooperate with means in the chamber defining an axial channel for receiving a corresponding flexible cover of a covered needle in said chamber to enable piercing of the diaphragm by the needle.

The chamber may be divided into compartments by a flexible intermediate wall forming a corresponding flexible lip or lips to that or those in the outer end wall and also serving to lightly grip a flexible needle cover or sleeve.

In a blood-sampling system including a stopper according to the invention, the pressure of the stopper lips on the side walls of the needle sleeve or cover retains the tube pre-assembled to the needle inside the needle holder. There is consequently no need for a partial perforation of the membrane to pre-assemble the tube and needle holder prior to use and, as a result the stopper membrane can be made quite thin. This reduction of the membrane thickness enables perforation of the membrane and disengagement of the membrane from the needle to be carried out with easy, rapid gests permitting a very gentle technique of blood sampling.

BRIEF DESCRIPTION OF THE DRAWINGS

Embodiments of the invention will now be described, by way of example, with reference to the accompanying drawings, in which:

FIG. 1a shows a variation of a detail of FIG. 1;

FIGS. 11 and 12 are schematic views of a blood sampling system including a stopper similar to that of FIG. 7, shown in two different positions;

DESCRIPTION OF THE PREFERRED EMBODIMENTS

Figure 1:
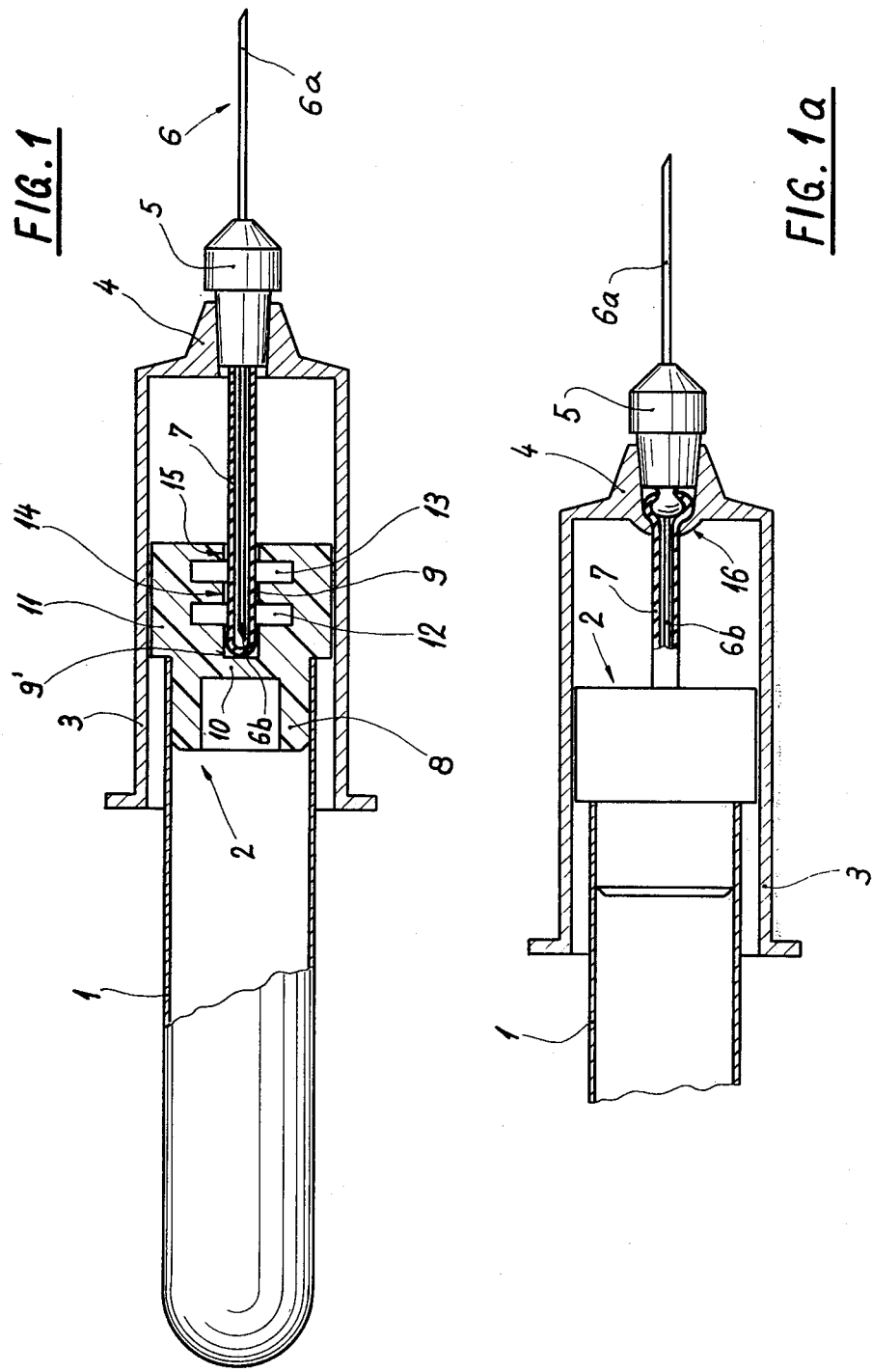
FIG. 1 is an axial cross-section of a blood sampling system including a first type of stopper.
Figure 2:
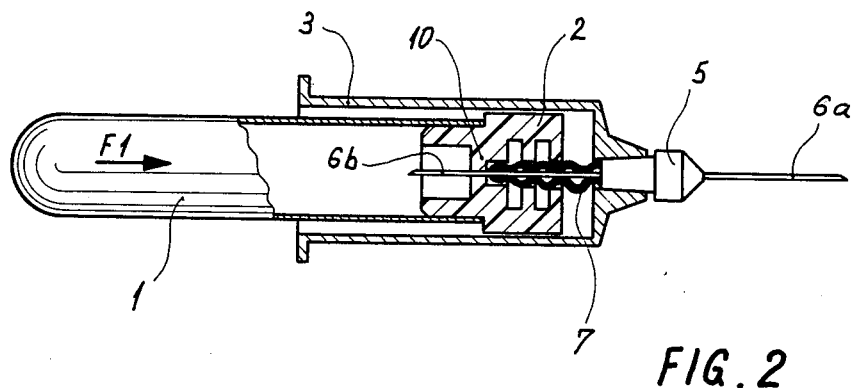
FIG. 2 shows the system of FIG. 1 in a position for taking in a blood sample.
Figure 3:
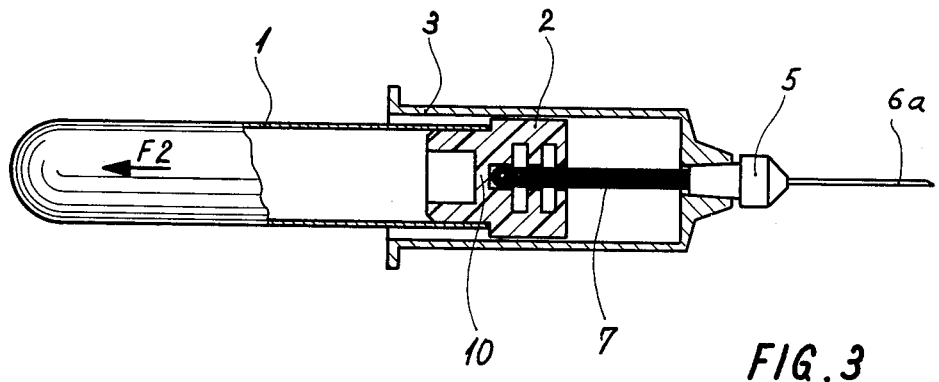
FIG. 3 shows the system of FIG. 1 in a rest position after taking a blood sample.

The blood sampling system shown in FIGS. 1 to 3 comprises an open-ended evacuated vial in the form of a tube 1 of glass or plastic material, hermetically closed by a stopper 2. A tubular needle-holder 3, slidably mounted on the stopper 2, has at one end a narrowed neck 4 receiving a ferrule 5 of plastic material carrying a hollow needle 6 extending along the axis of holder 3. One end 6a of this needle protrudes out of the neck 4 and serves to prick into a vein, and another end 6b is disposed inside the holder 3 encased in a loose sleeve or cover 7 of latex or flexible plastics material. As shown in the variation of FIG. 1a, the cover 7 may be fitted about a rounded head on the ferrule 5 and held against a corresponding rounded shoulder 16 of the neck 4.

The stopper 2 is formed by a body of deformable material such as synthetic rubber including a sealing portion in the form of a narrow shank 8 extending from a larger flange-forming head 11. The shank 8 is tightly fitted in the neck of tube 1, against the end of which the head 11 abuts. At the junction of head 11 and shank 8, the stopper 2 is closed by a thin membrane 10 from which a skirt forming the shank 8 extends. The head 11 is hollow and has a chamber of relatively large section, formed of two compartments 12 and 13. In this chamber is provided an axial channel 9 of reduced section leading to the membrane 10. The chamber compartments 12,13 are defined by inwardly-projecting flexible annular walls 14 and 15. The wall 15 forms an outer end wall of the stopper. The walls 14,15 have central circular openings defining, with a recess 9' of the same diameter leading to the membrane 10, the channel 9. The diameter of channel 9 is slightly less than the normal outer diameter of the needle cover 7 so that the inner parts (flexible annular lips) of the walls 14,15 hold the cover 7 with a slight inward pressure.

When the tube 1 is pressed in a direction F1 (FIG. 2), to prick the needle end 6a in a vein, the cover 7 is compressed and buckles as shown in FIG. 2 and the end 6b of the needle pierces membrane 10 whereupon blood is drawn into the tube 1. As shown, the cover 7 is able to buckle along substantially its entire length, including its part within the chamber compartments 12,13, so that the biasing force exerted by the cover 7 on the stopper 2 and tending to return it to its initial position is reduced, compared to that obtained in a conventional system in which buckling of the cover is confined over a short distance starting from the outer face of the stopper. The risk of jamming encountered in conventional systems when the flexible needle cover is fully compressed is also obviated. When the tube 1 is returned in direction F2 to the position of FIG. 3, the cover 7 automatically closes off the open end 6b of the needle, and prevents blood being projected onto the stopper 2. The lip-forming flexible walls 14,15 hold the cover 7 with a sufficient force to maintain the tube 1 in the rest position of FIG. 3. To remove the tube 1 and its stopper 2 from the holder 3, the operator simply has to exert a slight pull.

By suitably choosing the thickness of the membrane 10 and that of the cover 7, it is possible to arrange for the biasing force exerted by the buckled cover 7 to be slightly greater than the frictional resistance due notably to the pressure of the membrane 10 on the needle. In this manner, the tube 1 is automatically lightly biased to the rest position; once the tube 1 has been filled, the operator thus simply removes his thumb to allow disengagement of the stopper 2 from needle 1. The tube 1 then stops in its rest position by the slight gripping effect of the resilient walls 14,15 on the cover 7. This gripping force may be sufficient to hold the tube 1 in the holder 2, even when the holder 2 is held with the tube 1 down. Then the tube 1 can be pulled easily out of the holder 3.

Alternatively, it is possible to arrange for the gripping of the membrane 10 on the needle to cancel or approximately cancel the biasing effect of the buckled cover 7, if desired. This obviates the need for the operator to press on the tube 1 during blood sampling, and consequently eliminates the risk of the operator accidentally hurting the patient or traumatizing the vein.

During the sampling operation, the outer part of the head 11 of stopper 2 is never in contact with the bare end 6a of the needle and consequently cannot become covered with blood.

Figure 4:
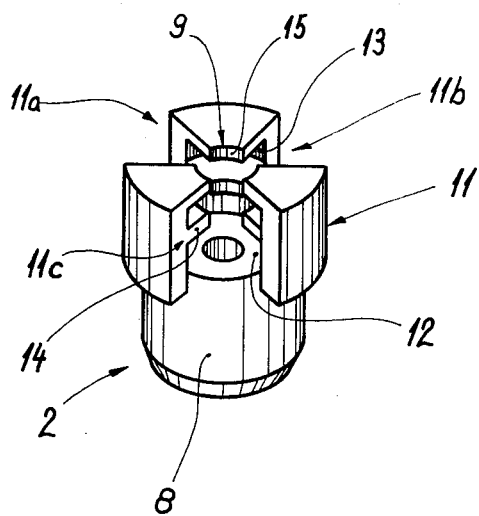
FIG. 4 is a perspective view of a second type of stopper.

FIG. 4 shows another form of stopper for the vial of a blood sampling system, the same reference designating the same parts as before. The stopper 2 comprises, as previously, a shank 8 and a head 11 with a central guide channel 9 defined by flexible walls 14,15, but in this embodiment the head 11 is divided into several equispaced segments, namely in this case three, separated by cutouts 11a, 11b, 11c which open into the chamber compartments 12,13. The outer end wall 15, as well as wall 14, thus forms three flexible lips or tongues each integral with a discrete portion of the peripheral wall of head 11. Alternatively, instead of dividing the head 11, into discrete segments, these cut-outs 11a, 11b, 11c may extend only partly into the peripheral walls of the stopper head, for example only very close to the top of the stopper head, or down to the middle of the head.

Figure 5:
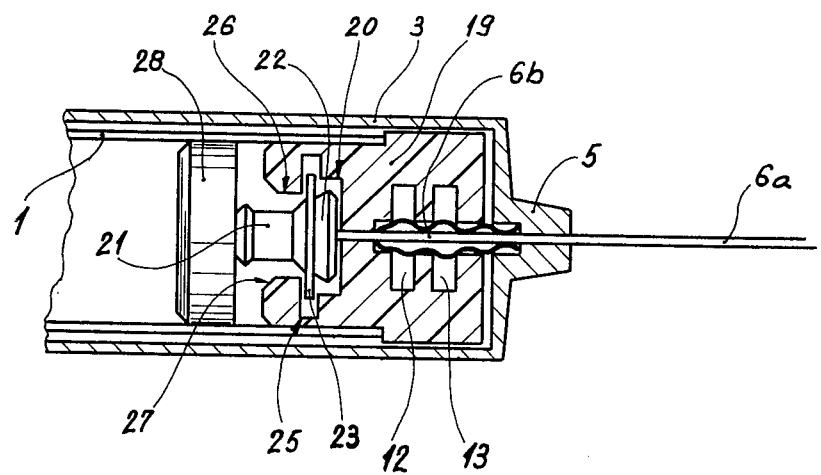
FIG. 5 is an axial cross-section of part of a blood sampling system including a third type of stopper.

In FIG. 5, where like parts are designated by the same references as before, a stopper 19 has at its rear end a shank fitting in the neck of tube 1, this shank including a skirt defining a recess 20 receiving an intermediate securing member 21 coupled to a piece 28. This piece 28 may serve to support auxiliary members such as filters, diffusers, means for isolating the contents of tube 1 from the stopper, and so on.

Member 21, shown in elevation, has a central bore for the passage of the liquid delivered via the needle, and a conical head 22 on which is a retaining annular flange 23. This flange 23 rests in an annular groove 25 for greater diameter and, when the stopper 19 is fitted in tube 1, is held by an inwardly projecting flange 26 having an opening of greater diameter than the shank of member 21. The outer face of flange 26 is chamfered to facilitate fitting of the member 21 by elastic deformation of the flange 26 when the stopper is not fitted in the tube 1. The member 21 (with its coupled piece 28) thus remains fixed to the stopper 19 when the latter is fitted in the tube 1, even during centrifuging, shaking and transport. Once the stopper 19 and member 21 have been extracted from the tube 1, the member 21 can be removed. The fixing of accessories in this manner enables the use of different techniques to those in which similar accessories were placed in tubes so as to be free to move during centrifuging etc. As an alternative, the member 21 could be secured releasably to the stopper 19 so that when the stopper is removed from the tube, the member 21 and its coupled piece 28 remain fixed in the tube.

Figure 6:
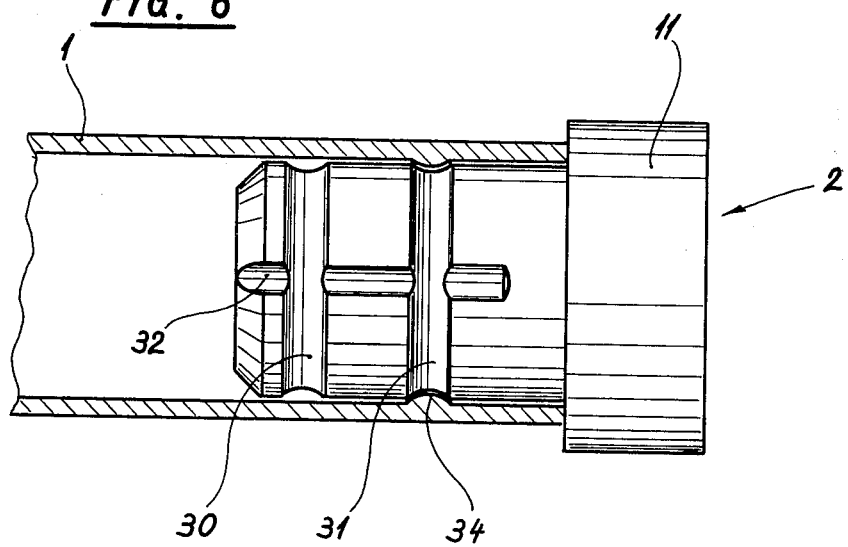
FIG. 6 is an elevational view of a fourth type of stopper fitted in a vial, shown in cross-section.

The stopper 2 shown in FIG. 6 comprises a head 11 provided, as before, with an inner chamber, but with a shank which has two external annular grooves 30,31 spaced apart from one another along the axis of the stopper and an external axially-extending groove 32 communicating with grooves 30,31 and extending from near the head 11 to the inner end of the stopper. More than one such axial groove may be provided. The grooves 30,31 are of arcuate section corresponding to an internal annular bulge 34 in the neck of tube 1, and are positioned so that when groove 31 engages on bulge or bead 34, the head 11 is against the end of the tube. In this position, the tube 1 is hermetically closed by the stopper. To increase the efficiency of this sealing, the annular grooves 30,31 are, as shown, deeper than the axial groove 32, although the sections of the grooves could be the same.

When the stopper 2 is pulled out so that the bulge 34 is between the annular grooves 30,31 and the axial groove 32 reaches the end of tube 1, air can flow along groove 32 so that, for example, the initially evacuated tube can be brought to atmospheric pressure.

When the stopper 2 is further pulled out to bring the bulge 34 into groove 30, the tube 1 is once more hermetically sealed.

This ventilation system enables the inside of tube 1 to be brought to atmospheric pressure before removal of the stopper, and consequently the avoidance of any "spring" effect as the stopper is pulled out, which in blood sampling tubes may cause an aerosol of blood to be projected, with the consequent risk of contamination. Also, the hermetic joint formed by bulge 34 keeps the outer part of the stopper shank clean and dry as it is permanently isolated from blood in the tube. When the stopper is removed it can consequently be manipulated with no great risk of contamination. The described ventilation system also enables the stopper to remain in the tube during the operations of evacuation, filling with blood and removal of the blood sample.

In applications other than blood sampling, the stopper of FIG. 6 enables a controlled transfer of the liquid in tube 1 by bringing it to the intermediate position with the bulge 34 between grooves 30 and 31. The outflow is stopped by pulling the stopper out to bring bulge 34 into groove 30. This immediately stops the flow whereas pushing the stopper in would firstly tend to accelerate the flow. Transfers can be effected in this manner in a vial or tube with two open ends each closed by such a stopper.

Figure 7:
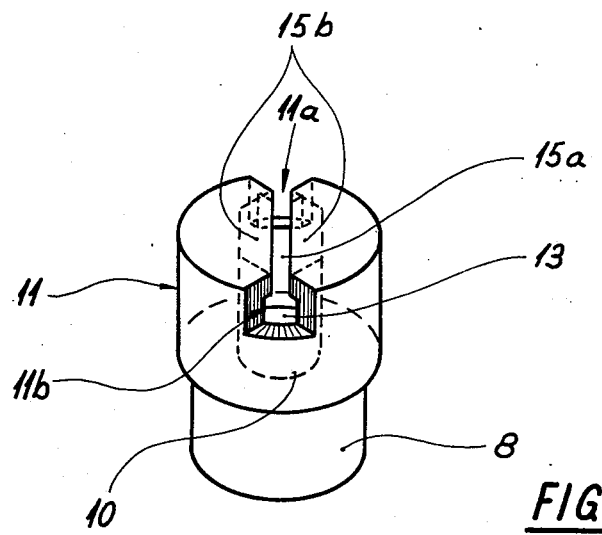
FIGS. 7, 8 and 9 are perspective views of further types of stopper.

The stopper of FIG. 7 comprises a sealing shank 8 and a flange-forming head 11 in which a single chamber 13 is defined by membrane 10, the peripheral wall of head 11 and a flexible upper wall 15 which is divided in two by a diametral slot 15a. At the ends of slot 15a, the peripheral wall of head 11 has a cut-outs 11a and 11b. The facing flexible lip-forming edges 15b of wall 15 may be of rectangular section, bevelled inwardly or outwardly, rounded (either concave or convex) or triangular.

Figure 8:
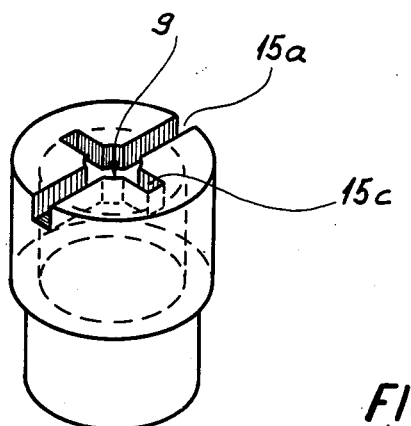

In the variation of FIG. 8, a diametral slot 15a is intersected by a shorter slot 15 to leave a cruciform opening defining four flexible lips or tongues whose inner ends are shaped to form a generally circular central opening 9a for receiving a needle sheath.

Figure 9:
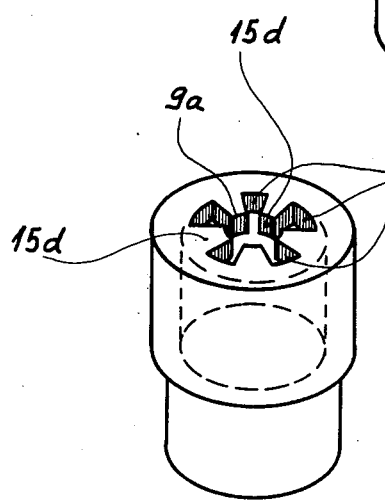

The varied stopper of FIG. 9 has, in the outer end wall 15, five inwardly-directed flexible lips or tongues 15d separated by segment-shaped openings 15e, the flexible inner ends of the lips or tongues 16d being disposed about a generally circular opening 9a.

Figure 10:
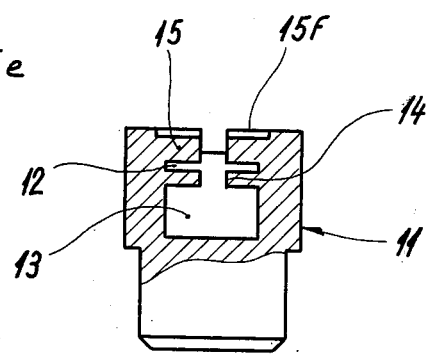
FIG. 10 is a cross-section through another stopper.

FIG. 10 shows a variation of the stopper of FIGS. 7 to 9 in which there is a flexible intermediate wall 15 in the chamber 13 to define a second compartment 12, as before. Also, in this variation, the lip-forming outer wall 15 is inset by a circular recess 15f in the outer face of head 11.

Figure 13:
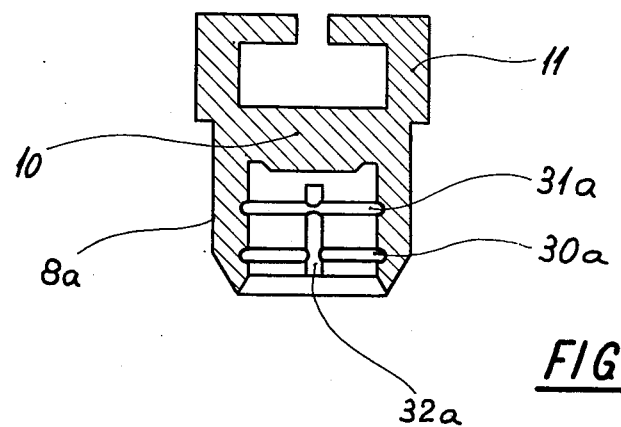
FIG. 13 is a cross-section of yet another form of stopper.

FIGS. 11 and 13 show a stopper similar to that of FIG. 7, but with rounded edges 15b, used to obturate a tube 1 fitted in a blood sampling system, of which only needle holder 3 and needle cover 7 are shown. These Figures show how the lip-forming edges 15b, which are made very flexible by the cut-outs 11a and 11b, deform and elastically grip the cover 7. Also, FIG. 12 shows how the single chamber 13 can accommodate a relatively great buckling of the cover 7 and effectively cancel the biasing effect of the deformed cover. With this arrangement, the zone along which the cover 7 can be compressed may be about 60% greater than with conventional compact stoppers. By increasing the zone of compression of the cover 7 in the chamber 13, and allowing the cover to expand freely outwardly into the chamber 13, an excessive gripping of the cover 7 on the needle is avoided. As can be seen on FIG. 12, the part of cover 7 which remains outside the chamber 13 is practically not compressed at all.

Figure 14:
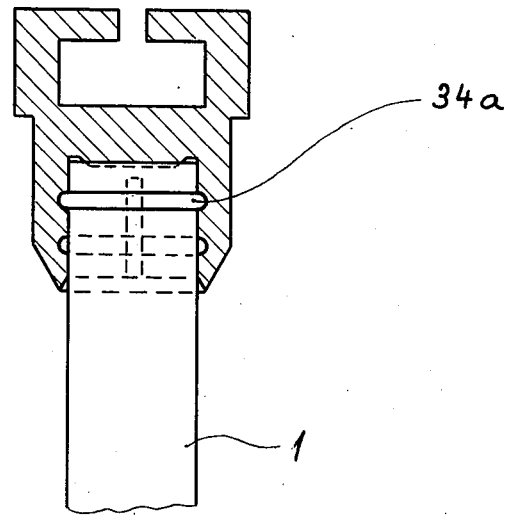
FIG. 14 shows the stopper of FIG. 13 fitted on a vial.

The stopper of FIGS. 13 and 14 comprises a sealing skirt 8a extending from a head 11 and membranes 10. This skirt differs from the previous embodiments in that it is adapted to fit over the end of a tube 1, as shown in FIG. 14, instead of inside. The inner cylindrical face of skirt 8a has two annular grooves 30a,31a and an axially directed groove 32a analogous to the previous grooves 30,31,32 of FIG. 6, the grooves 30a,31a being able to cooperate with an external annular bulge or bead 34a on the neck of tube 1. As before, the groove 31a is deeper than groove 32a to provide a sealing engagement; however, the groove 30a is shallower than groove 32a, so that when groove 30a engages on the bulge 34a it defines a ventilating position. This provides a similar ventilation system as described with reference to FIG. 6, except that there is not a pulled-out sealing position. The stopper of FIG. 14 has the advantage that blood in the tube cannot contact its outer surface so that there is no risk of contamination when handling the stopper. Also, this stopper can be used with vials or tubes having a neck of small diameter.

What is claimed is:

1. A generally cylindrical stopper for a vial comprising, a hollow body of deformable material having a peripheral wall and insertable into the neck of a vial, a closed inner end wall defining a thin sealing diaphragm to obturate the vial, and a flexible outer end wall defining at least one flexible lip delimiting at least one slot, said at least one lip extending radially inwardly from said peripheral wall and defining a central opening of relatively small cross-sectional area leading into a chamber of larger cross-sectional area and defined by said end and peripheral walls.

2. A stopper according to claim 1 comprising, a head which cannot penetrate the vial and an integral sealing portion extending from said head for providing a sealing fit with the neck of a vial, and in which said chamber is located wholly within said head.

3. A stopper according to claim 1, in which said central opening is generally circular, including means in said chamber defining with said central opening an axial channel for receiving through said central opening a corresponding flexible sleeve of a covered needle extending into said chamber to enable piercing of said diaphragm by said needle.

4. A stopper according to claim 3, in which said outer end wall forms at least one first flexible lip and said means in said chamber comprise at least one corresponding second flexible lip integral with and extending inwardly from said peripheral wall to divide said chamber into two coaxial compartments, said first and second lips having flexible inner ends delimiting corresponding central openings defining said axial channel.

5. A stopper according to claim 2, in which said head is divided into a plurality of segments, each segment having an outer end wall portion defining a flexible lip integral with a peripheral wall portion, the adjacent segments being spaced apart by slots to open said chamber to the exterior of the stopper head.

6. A stopper according to claim 1, comprising a head which cannot penetrate the neck of the vial and an integral sealing portion extending from said head for providing a sealing fit with the neck of the vial, and further comprising means defining at least one axially-directed groove and at least one annular groove in a surface of said sealing portion for cooperation with vial neck, said at least one said annular groove being configured in cross section to receive therein a corresponding annular bead of the vial neck to provide a sealing fit, and said stopper being outwardly movable from the vial from a position in which there is a sealing fit to a position in which said axially-directed groove communicates the interior of the vial with the exterior.

7. A stopper according to claim 6, in which said axially-directed groove(s) is (are) of shallower section than said at least one annular groove.

8. A stopper according to claim 6, comprising spaced-apart first and second annular grooves each able to cooperate with said bulge to provide a sealing fit.

9. A stopper according to claim 6, comprising a first said annular groove of section no shallower than that of said at least one axially-directed groove to be able to provide said sealing fit, and a second annular groove of shallower section than said axially-directed groove, said second annular groove being able to cooperate with said bulge to define said position of the stopper in which said axially directed groove communicates the interior of the vial with the exterior.

10. A stopper according to claim 1, in which said flexible outer end wall of the head is divided into said at least one flexible lip by a diametrical slot defining said central opening.

11. A stopper according to claim 10, in which said diametrical slot extends across the entire extent of said end wall and divides it into two flexible lips, and comprising at least one end of said diametrical slot an opening in said peripheral wall of said head.

12. A stopper according to claim 10, comprising at least one second slot crossing said diametrical slot centrally to define at their intersection said central opening.

13. A stopper according to claim 2, in which said outer end wall of said head comprises at least three like flexible lips or tongues separated by segment-like radial slots, said lips or tongues having flexible inner ends disposed about and defining said central opening.

14. A stopper according to claim 1, comprising a head which cannot penetrate the neck of the vial and an integral sealing portion extending from said head for providing a sealing fit with the neck of a vial, and in which said sealing portion comprises a skirt extending from said head for sealably fitting circumferentially about the neck of the vial.

15. A stopper according to claim 6, in which said sealing portion comprises a skirt extending from said head for sealably fitting over the neck of a vial, said grooves being provided in an inner surface of said skirt whereby said annular grooves are able to cooperate with an external annular bulge on a vial neck.

16. A stopper according to claim 14, in which said skirt has at least one annular groove in its inner surface configured in cross section to receive a corresponding annular external bead on the vial neck to provide a position in which said bead is embedded in said annular groove, said skirt further extending beyond said groove in a tight seal zone for fitting circumferentially about the neck of the vial.

17. A stopper according to claim 14, in which said skirt has at least one axially directed groove in its inner surface.

18. A stopper according to claim 1, having at least two interconnected slots dividing said flexible outer end wall into a plurality of flexible lips.

19. A stopper according to claim 1, having at least one side opening extending from an upper part of the peripheral wall transversely across the outer end wall splitting it to form said flexible lips defining said central opening.

20. A stopper according to claim 1 in combination with a blood-sampling needle assembly comprising a needle-holder slidably mounted on the stopper, a hollow needle having a first end part extending axially in said holder and a second end part protruding from said holder, and a flexible needle sleeve covering said first end part of the needle, said needle sleeve fitting loosely about the needle and being receivable in said central opening of said outer end wall in touching engagement with said flexible lips whereby the needle assembly and stopper can be held together by engagement of said flexible lips and said needle sleeve, said needle sleeve being resiliently deformable within said chamber to allow movement of said holder and needle relative to the stopper whereby said first end part of the needle pierces said needle cover and said membrane.

* * * * *